(12) United States Patent
Rebec et al.

(10) Patent No.: US 8,452,357 B2
(45) Date of Patent: *May 28, 2013

(54) NON-INVASIVE METHODS OF USING SPECTRAL INFORMATION IN DETERMINING ANALYTE CONCENTRATIONS

(75) Inventors: Mihailo V. Rebec, Bristol, IN (US); Michael P. Houlne, Centennial, CO (US)

(73) Assignee: Bayer HealthCare LLC, Tarrytown, NY (US)

( * ) Notice: Subject to any disclaimer, the term of this patent is extended or adjusted under 35 U.S.C. 154(b) by 902 days.

This patent is subject to a terminal disclaimer.

(21) Appl. No.: 12/575,802

(22) Filed: Oct. 8, 2009

(65) Prior Publication Data

US 2010/0022860 A1 Jan. 28, 2010

Related U.S. Application Data

(63) Continuation of application No. 11/894,510, filed on Aug. 21, 2007, now Pat. No. 7,603,151.

(60) Provisional application No. 60/839,299, filed on Aug. 22, 2006.

(51) Int. Cl.
*A61B 5/1455* (2006.01)

(52) U.S. Cl.
USPC ............................ 600/310; 600/316; 600/322

(58) Field of Classification Search
USPC ......................................... 600/310, 316, 322
See application file for complete search history.

(56) References Cited

U.S. PATENT DOCUMENTS

| | | | |
|---|---|---|---|
| 4,634,276 A | 1/1987 | Sharpe | 356/305 |
| 4,645,340 A | 2/1987 | Graham et al. | 356/301 |
| 5,560,356 A | 10/1996 | Peyman | 600/316 |
| 5,615,673 A | 4/1997 | Berger et al. | 128/633 |
| 5,754,289 A | 5/1998 | Ozaki et al. | 356/301 |
| 5,923,482 A | 7/1999 | Gilby | 359/846 |
| 6,044,285 A | 3/2000 | Chaiken et al. | 600/316 |
| 6,070,093 A | 5/2000 | Oosta et al. | 600/316 |
| 6,137,641 A | 10/2000 | Gilby | 359/846 |

(Continued)

FOREIGN PATENT DOCUMENTS

| | | |
|---|---|---|
| EP | 0 129 289 B1 | 9/1990 |
| EP | 0 636 232 B1 | 1/1998 |

(Continued)

OTHER PUBLICATIONS

Z. Huang, H. Zeng, I. Hamzavi, D. McLean, and H. Lui, "Rapid Near-Infrared Raman Spectroscopy System for Real-Time In Vivo Skin Measurements", Optics Letters, 26 (22), 1782-1784 (2001).

(Continued)

*Primary Examiner* — Eric Winakur
(74) *Attorney, Agent, or Firm* — Nixon Peabody LLP

(57) ABSTRACT

A non-invasive method of determining the concentration of an analyte uses Raman or fluorescence spectral information. A high-intensity band of light is applied to one side of skin tissue. The high-intensity light enters the skin tissue and generates a Raman or fluorescence signal. A Raman-generating material or fluorescence-generating material is placed in a location nearest the other side of skin tissue. The Raman-generating or fluorescence-generating material is located generally opposite of the entry of the applied high-intensity light. The Raman or fluorescence signal is collected and the analyte concentration is determined using the collected Raman signal.

52 Claims, 7 Drawing Sheets

U.S. PATENT DOCUMENTS

| | | | | |
|---|---|---|---|---|
| 6,167,290 | A | 12/2000 | Yang et al. | 600/322 |
| 6,223,063 | B1 | 4/2001 | Chaiken et al. | 600/310 |
| 6,289,230 | B1 | 9/2001 | Chaiken et al. | 600/322 |
| 6,292,686 | B1 | 9/2001 | Chaiken et al. | 600/476 |
| 6,332,092 | B1 | 12/2001 | Deckert et al. | 600/476 |
| 6,352,502 | B1 | 3/2002 | Chaiken et al. | 600/4.73 |
| 6,377,828 | B1 | 4/2002 | Chaiken et al. | 600/316 |
| 6,389,306 | B1 | 5/2002 | Chaiken et al. | 600/474 |
| 6,486,948 | B1 | 11/2002 | Zeng | 356/301 |
| 6,503,478 | B2 | 1/2003 | Chaiken et al. | 429/9.1 |
| 6,560,478 | B1 | 5/2003 | Alfano et al. | 600/473 |
| 6,574,490 | B2 | 6/2003 | Abbink et al. | 600/316 |
| 6,615,061 | B1 | 9/2003 | Khalil et al. | 600/310 |
| 6,636,305 | B2 | 10/2003 | Zhao et al. | 356/300 |
| 6,681,133 | B2 | 1/2004 | Chaiken et al. | 600/473 |
| 6,690,966 | B1 | 2/2004 | Rava et al. | 600/473 |
| 7,308,293 | B2 | 12/2007 | Gerlitz | 600/318 |
| 2003/0023170 | A1 | 1/2003 | Gardner et al. | 600/476 |
| 2003/0071993 | A1 | 4/2003 | Zhao et al. | 356/300 |
| 2003/0120137 | A1 | 6/2003 | Pawluczyk | 600/310 |
| 2004/0152992 | A1 | 8/2004 | Zeng | 600/476 |
| 2005/0043597 | A1 | 2/2005 | Xie | 600/315 |

FOREIGN PATENT DOCUMENTS

| | | |
|---|---|---|
| WO | WO 2003/023339 A1 | 3/2003 |
| WO | WO 2003/056311 A1 | 7/2003 |
| WO | WO 2004/023125 A2 | 3/2004 |
| WO | WO 2004/064627 A1 | 8/2004 |
| WO | WO 2006/127766 A1 | 11/2006 |

OTHER PUBLICATIONS

"A Noninvasive Glucose Monitor: Preliminary Results in Rabbits" by Mark S. Borchert, M.D., et al., *Diabetes Technology & Therapeutics*, vol. 1, No. 2, 1999, Mary Ann Liebert, Inc. (pp. 145-151).

"Laser-Based Measurement of Glucose in the Ocular Aqueous Humor: An Efficacious Portal for Determination of Serum Glucose Levels" by Paul G. Steffes, Ph.D., *Diabetes Technology & Therapeutics*, vol. 1, No. 2, 1999, Mary Ann Liebert, Inc. (pp. 129-133).

Written Opinion corresponding to International Patent Application No. PCT/US2007/018310, European Patent Office, dated Sep. 29, 2008, 10 pages.

International Search Report corresponding to International Patent Application No. PCT/US2007/018310, European Patent Office, dated Sep. 29, 2008, 5 pages.

NON-INVASIVE METHODS OF USING SPECTRAL INFORMATION IN DETERMINING ANALYTE CONCENTRATIONS

CROSS-REFERENCE TO RELATED APPLICATION APPLICATIONS

This application is a continuation application of U.S. patent application Ser. No. 11/894,510 filed Aug. 21, 2007, which claims priority to U.S. Provisional Application Ser. No. 60/839,299 filed on Aug. 22, 2006, both of which are incorporated by reference in their entireties.

FIELD OF THE INVENTION

The present invention generally relates to a method of determining the concentration of an analyte. More specifically, the present invention is directed to a non-invasive method of determining the concentration of an analyte using spectral information (e.g., Raman or fluorescence).

BACKGROUND OF THE INVENTION

The quantitative determination of analytes in body fluids is of great importance in the diagnoses and maintenance of certain physiological abnormalities. For example, lactate, cholesterol and bilirubin should be monitored in certain individuals. In particular, determining glucose in body fluids is important to diabetic individuals who must frequently check the glucose level in their body fluids to regulate the glucose intake in their diets. The results of such tests can be used to determine what, if any, insulin or other medication needs to be administered.

Determining the analyte concentration of, for example, glucose is typically performed by invasive methods. It would be desirable to determine analyte concentrations by using a non-invasive method.

Non-invasive methods may incorporate the use of different types of signals to determine the analyte concentration. One type of signal is a Raman spectral signal. The use of Raman spectral information, however, has had limited application in determining non-invasive analyte concentrations because the signals tend to be very weak. There are a number of factors that contribute to the very weak Raman signal collected from the skin. One factor is the limited amount of high-intensity energy that one can safely deliver into tissue without causing photo-damage to the tissue. A second factor is the limited Raman scattering efficiency inherent to most molecules of analytical and physiological interest. A third factor is the scattering and absorbance characteristics of the tissue that limit the amount of energy that can be effectively delivered into the tissue and the amount of Raman spectral information that can be collected from the tissue.

Another type of signal is a fluorescence signal, which like Raman signals also has disadvantages. Fluorescence signals are more general in nature than Raman signals. Fluorescence molecules of interest may be of a smaller number than desired. The scattering and absorbance characteristics of the tissue limit the amount of energy that can be effectively delivered into the tissue and the amount of fluorescence spectral information that can be collected from the tissue.

Optical absorbance and tissue scattering, which are two fundamental optical properties of tissue, can be transient during non-invasive detection of an analyte such as glucose. Optical absorbance and tissue scattering can affect the glucose concentration measurement.

It would be desirable to develop a non-invasive method using spectral information such as Raman or fluorescence spectral information that more accurately determines the analyte concentration.

SUMMARY OF THE INVENTION

According to one non-invasive method, the concentration of an analyte is determined using Raman spectral information. A high-intensity, narrow band of light is applied to a first side of skin tissue. The high-intensity light enters the skin tissue and generates a Raman signal. A Raman-generating material is placed in a location nearest a second side of the skin tissue. The second side is located generally opposite of the first side. The high-intensity light is reflected from the Raman-generating material so as to produce additional Raman signal that passes through the skin tissue towards the first side of the skin tissue. The Raman signal generated from the high-intensity light entering the skin tissue is reflected towards the first side of the skin tissue via the Raman-generating material. The Raman signal generated from the high-intensity light entering the skin tissue and the additional Raman signal generated from the Raman-generating material is collected. The analyte concentration using information from the collected Raman signals is determined.

According to another non-invasive method, a diagnosis using Raman spectral information is determined. A high-intensity, narrow band of light is applied to a first side of skin tissue. The high-intensity light enters the skin tissue and generates a Raman signal. A Raman-generating material is placed in a location nearest a second side of the skin tissue. The second side is located generally opposite of the first side. The high-intensity light is reflected from the Raman-generating material so as to produce additional Raman signal that passes through the skin tissue towards the first side of the skin tissue. The Raman signal generated from the high-intensity light entering the skin tissue is reflected towards the first side of the skin tissue via the Raman-generating material. The Raman signal generated from the high-intensity light entering the skin tissue and the additional Raman signal generated from the Raman-generating material is collected. Information from the collected Raman signals is used to perform a general diagnosis.

According to a further non-invasive method, the concentration of an analyte using Raman spectral information is determined. An area of the skin tissue is pinched. A Raman-generating material is placed near or around the pinched skin tissue. The Raman-generating material forms at least one opening therethrough. A high-intensity, narrow band of light is applied to the skin tissue through the at least one opening. The high-intensity light enters the skin tissue and generates a Raman signal. The high-intensity light and Raman signal that pass through the pinched skin tissue is reflected back into the pinched skin tissue via the Raman-generating material. The Raman signal generated from the high-intensity light entering the skin tissue and the additional Raman signal generated from the Raman-generating material is collected. The analyte concentration is determined using the collected Raman signals.

According to a non-invasive method, the concentration of an analyte using fluorescence spectral information is determined. A high-intensity, narrow band of light is applied to a first side of skin tissue. The high-intensity light enters the skin tissue and generates a fluorescence signal. A fluorescence-generating material is placed in a location nearest a second side of the skin tissue. The second side is located generally opposite of the first side. The high-intensity light is reflected from the fluorescence-generating material so as to produce additional fluorescence signal that passes through the skin tissue towards the first side of the skin tissue. The fluorescence signal generated from the high-intensity light entering the skin tissue is reflected towards the first side of the skin tissue via the fluorescence-generating material. The fluorescence signal generated from the high-intensity light entering the skin tissue and the additional fluorescence signal generated from the fluorescence-generating material is collected. The analyte concentration using information from the collected fluorescence signals is determined.

According to another non-invasive method, a diagnosis using fluorescence spectral information is performed. A high-intensity light is applied to a first side of skin tissue. The high-intensity light enters the skin tissue and generates a fluorescence signal. A fluorescence-generating material is placed in a location nearest a second side of the skin tissue. The second side is located generally opposite of the first side. The high-intensity light is reflected from the fluorescence-generating material so as to produce additional fluorescence signal that passes through the skin tissue towards the first side of the skin tissue. The fluorescence signal generated from the high-intensity light entering the skin tissue is reflected towards the first side of the skin tissue via the fluorescence-generating material. The fluorescence signal generated from the high-intensity light entering the skin tissue and the additional fluorescence signal generated from the fluorescence-generating material is collected. Information from the collected fluorescence signals is used to perform a general diagnosis.

According to a further non-invasive method, the concentration of an analyte using fluorescence spectral information is determined. An area of the skin tissue is pinched. A fluorescence-generating material is placed near or around the pinched skin tissue. The fluorescence-generating material forms at least one opening therethrough. A high-intensity, narrow band of light is applied to the skin tissue through the at least one opening. The high-intensity light enters the skin tissue and generates a fluorescence signal. The high-intensity light and fluorescence signal that pass through the pinched skin tissue back is reflected into the pinched skin tissue via the fluorescence-generating material. The fluorescence signal generated from the high-intensity light entering the skin tissue and the additional fluorescence signal generated from the fluorescence-generating material is collected. The analyte concentration using the collected fluorescence signals is determined.

BRIEF DESCRIPTION OF THE DRAWINGS

FIG. 6b is an illustration further detailing the spatial filter used in determining the analyte concentration of FIG. 6a.

DETAILED DESCRIPTION OF THE ILLUSTRATED EMBODIMENTS

In one method, the invention is directed to non-invasive methods for determining the concentration of an analyte uses Raman spectral information. The invention is adapted to increase optical throughput in these methods using spectral information. Analytes that may be measured using the Raman spectral information include glucose, lipid profiles (e.g., cholesterol, triglycerides, LDL and HDL), microalbumin, hemoglobin $A_{1C}$, fructose, lactate, or bilirubin. The present invention is not limited, however, to these specific analytes and it is contemplated that other analyte concentrations may be determined. The analytes may be in, for example, a whole blood sample, a blood serum sample, a blood plasma sample, and other body fluids like ISF (interstitial fluid) and urine.

The present invention assists in providing a method of correcting for optical absorbance and/or tissue scattering that can be transient during non-invasive analyte (e.g., glucose) detection. The Raman signature of analytes such as glucose can be corrected based on the optical absorbance and tissue scattering occurring in the tissue. The absorption of the skin tissue and tissue scattering may vary in the short term, as well as the long term. For example, one non-limiting short-term situation could be increased blood flow or changes in the tissue hydration. One non-limiting long-term condition could be an individual's skin being tan or even burned. It is contemplated that the absorption of the skin tissue and tissue scattering may vary under other short-term and long-term conditions such as localized hematocrit, tissue deformity (e.g., scar or melanoma), temperature, pH or skin morphology.

According to one method, the concentration of an analyte is determined using Raman spectral information. A high-intensity, narrow band of light is applied to a first side of skin tissue. The high-intensity light enters the skin tissue and generates a Raman signal. A Raman-generating material is placed in a location nearest a second side of skin tissue. The second side is located generally opposite of the first side. The high-intensity light from the Raman-generating material is reflected so as to produce additional Raman signal that passes through the skin tissue towards the first side of the skin tissue. The Raman signal generated from the high-intensity light entering the skin tissue is reflected towards the first side of the skin tissue via the Raman-generating material. The Raman signal generated from the high-intensity light entering the skin tissue and the additional Raman signal generated from the Raman-generating material are collected. The analyte concentration is determined using information from the collected Raman signals.

Figure 1:
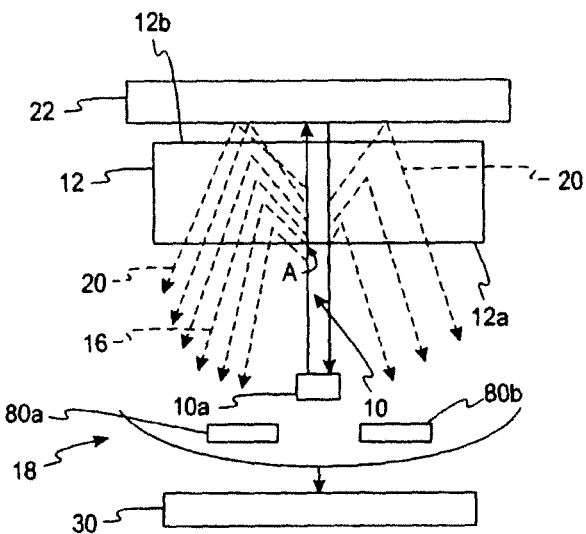
FIG. 1 is an illustration used in determining the concentration of an analyte using Raman spectral information according to one embodiment.

Referring to FIG. 1, an illustration is used showing the location of the Raman-generating material and the high-intensity, narrow band of light according to one method. High-intensity light 10 is applied to skin tissue 12 such as pinched skin tissue or a finger. The high-intensity light 10 is shown in FIG. 1 as coming from a high-intensity light source 10a. The high-intensity light source may be a variety of light sources. For example, the high-intensity light source may come from a monochromatic light source that is delivered in a narrow band. One example of a monochromatic light source is a laser-diode source. It is contemplated that other light sources may be used such as a light-emitting diode and incoherent lamps. The light sources may be filtered to provide a more clearly defined (i.e., narrow) band of light. It is also contemplated that the high-intensity light may be a dye laser, gas laser, ion laser or a pumped laser.

The wavelength of the light source may vary but is generally from about 300 to about 10,000 nm. The light source may be an ultraviolet light source, a near-infrared light source, an infrared light source, or visible light source with appropriate filtering. The light source to be used would be a high-intensity, narrow band of light.

The Raman spectral information in one method may be collected in the wavelength range from about 300 nm to about 12,000 nm. However, several wavelength-dependent characteristics unique to tissue optics and to the Raman effect can significantly impact the ability to successfully employ the Raman technique for the non-invasive determination of analytes in tissue. For example, at lower wavelengths, the inherent Raman signal from analytes in tissue is relatively strong, but tissue autofluorescence is also relatively strong, which may overwhelm and complicate detecting the Raman signal in the tissue. Conversely, at higher wavelengths, tissue autofluorescence and the inherent Raman signal decrease. The choice of the light source would be made based on a balance of the Raman signal power and the autofluorescence interference at the wavelengths of interest for the analyte of interest. Therefore, for glucose analysis, it is desirable to employ a high-intensity, narrow band light source centered at or near 830 nm and collect the Raman spectral information in the wavelength range of from above 830 nm to about 1030 nm where the strength of the Raman signal is optimized verses the tissue autofluorescence.

The glucose-related Raman spectral information may be collected from Raman scattered light shifted from 100 cm$^{-1}$ to 10,000 cm$^{-1}$ away from the light source. More specifically, the glucose-related Raman spectral information may be collected from Raman scattered light shifted from 100 cm$^{-1}$ to 1600 cm$^{-1}$ away from the light source since the strongest glucose peaks occur at Raman shifts of about 1340 cm$^{-1}$ and about 1125 cm$^{-1}$. It is contemplated that the Raman spectral information may be collected in different ranges, especially if the analyte concentration to be determined is not glucose.

One specific example is an 830 nm laser-diode source. One example of a commercially available 830 nm laser-diode source is Invictus™ NIR 830 nm diode laser, which is marketed by Kaiser Optical Systems, Inc. of Ann Arbor, Mich. Another example is a PI-ECL-830-300 diode laser, which is marketed by Process Instruments of Salt Lake City, Utah. In one embodiment, the laser light is delivered to the skin tissue in about a 1 mm beam diameter. It is contemplated that other laser-diode sources may be employed.

The high-intensity, narrow band of light may be adjusted so that a higher resolution Raman spectrum is generated. For example, the high-intensity narrow band of light may be limited, resulting in less light being exposed and a higher resolution Raman signal being obtained. By adjusting the high-intensity, narrow band of light, the strength of the Raman signal and the exposure may be optimized depending on the analyte of interest.

The high-intensity light 10 enters on a first side 12a of the skin tissue 12. The thickness of the skin tissue that may be used in determining the analyte concentration may vary. The skin tissue is generally from about 1 to about 5 mm in thickness. More specifically, the skin is generally from about 1 to about 3 mm in thickness. The skin tissue may be pinched when the high-intensity light enters the skin tissue.

As shown in FIG. 1, the high-intensity light 10 enters the skin tissue 12 at point A. After the high-intensity light 10 enters the skin tissue 12, a Raman signal is generated and scatters in all directions. A portion of the high-intensity light may contact the skin without entering the skin and scatter in all directions. A portion 16 of the Raman signal is redirected back towards collection optics 18 after entering the skin tissue 12. Some of the Raman signal exits the skin tissue 12, however, and is reflected back using a Raman-generating material 22. The Raman-generating material 22 reflects back Raman signals towards the collection optics 18 that would otherwise have been lost exiting the other side 12b of the skin tissue 12, which is opposite of the collection optics 18. Thus, an increased fraction of the Raman signal will be redirected to the collection optics 18. It is contemplated that an increased fraction of the Raman signal may be redirected using a reflective surface such as a mirror. A portion of the Raman signal created by the Raman-generating material is scattered at oblique angles and will not be detected or may also be absorbed before being detected.

The Raman-generating material 22 is placed in a location nearest the other side 12b of the skin tissue 12. The Raman-generating material is located generally opposite of the entry of the applied high-intensity light. As shown in FIG. 1, the Raman-generating material 22 is located opposite of the entry of the high-intensity light 10 at point A in FIG. 1. It is contemplated that the Raman-generating material may be a single reflector as shown in FIG. 1 or a plurality of reflectors.

The Raman-generating material 22 also receives the high-intensity light 10 and generates additional Raman signal therefrom. To the extent that the Raman-generating material does not create Raman signals from the high-intensity light 10, the Raman-generating material 22 reflects back the remaining portion of the high-intensity light back through the skin tissue 12. These Raman signals will typically envelop a larger volume of skin tissue because the Raman signals will originate and scatter outwardly from every point in the skin tissue. After this high-intensity light is reflected back into the skin tissue 12 via the Raman-generating material 22, additional Raman signals may be generated. Thus, the optical pathlength is increased by passing the source light through the skin tissue twice. By increasing the optical pathlength, the resulting analytical signal is also increased.

Using the Raman-generating material 22, a measure of optical absorption can be obtained. Absorption is generally proportional to the total quantity of Raman signal from the Raman-generating material 22 that passes through the sample. In the case where the entire Raman signal can be integrated, then the analytical signal can be further corrected for changes in tissue absorbance and tissue scattering. Changes in tissue absorbance and scattering may be caused by, for example, increased blood flow or changes in tissue hydration. For example, the intensity of the Raman signals from the Raman-generating material using only the high-intensity light can be compared to the intensity of the Raman signals using the Raman-generating material and the body tissue using the high-intensity light. A comparison of these intensities can determine and quantify the level of optical absorbance by the tissue. The level of optical absorbance can be done on an absolute basis or a relative basis. If done on an absolute basis, the high-intensity light will typically need to be adjusted to have a similar intensity level when contacting the Raman-generating material 22.

Thus, in summary, the Raman-generating material 22 (a) reflects back Raman signal created on the initial pass through the skin tissue that otherwise would have been lost; (b) creates Raman signal from the high-intensity light 10; and (c) reflects back the light source that did not create a Raman signal back into the skin tissue with the possibility of forming an additional Raman signal. These Raman signals are designated generally in FIG. 1 as Raman signals 20.

The Raman-generating material may be formed from a variety of materials. For example, the Raman-generating material may include a polymeric material such as Spectralon™ polymeric lining. Spectralon™ polymeric lining is a thermoplastic resin with a very high diffuse reflectance. Spectralon™ polymeric lining is available through Labsphere Inc. of North Sutton, N.H.

It is contemplated that other materials may be used as the Raman-generating material including other polymeric materials. For example, the Raman-generating material may include a polystyrene surface or polycarbonate surface. The Raman-generating material to be used needs to generate a unique Raman signal.

In one embodiment, the Raman-generating material may be a thin coating or layer on a thicker substrate, which is not a Raman-generating material. In another embodiment, the substrate may be formed entirely of the Raman-generating material.

Determining the concentration of an analyte (e.g., glucose) requires a measure proportional to the quantity of the analyte and a measure of the volume in which that quantity analyte resides. Employing a measure of optical scattering allows the analyte concentration calculation to be corrected should the optical probe volume change over the course of several measurements.

In one method, before collecting the Raman signals, a spatial filter is provided that measures the optical scattering of the Raman signals in the tissue. The amount of scattering affects the probe volume of the body tissue. The use of a spatial filter differentiates scattering from absorbance and further approximates the relative changes in absorbance and scattering in a skin tissue sample of fixed thickness.

In one method, a spatial filter is placed to block a fraction of the Raman signals emerging from the skin tissue and to allow the remaining fraction of the Raman signals to strike the at least one detector. Thus, a spatial filter blocks light in one portion and allows light through in another portion. FIG. 1 depicts a spatial filter 80, which is shown in more detail in FIG. 2a. The spatial filter 80 includes a plurality of apertures 82, 84, 86 being formed. Sections 80a, 80b of the spatial filter 80 block a fraction of the Raman signals. If the optical scattering is low, the intensity (I) of the Raman signal at the middle aperture 84 would likely be significantly higher than the intensities of the Raman signals at outer apertures 82, 86 since a small fraction of the Raman signals would take a lateral trajectory through the skin tissue.

In the scenario with optical scattering being low, a ratio of the intensity of Raman light through the right aperture 86 ($I_r$) to the intensity of the Raman light through the middle aperture 84 ($I_m$) after correction for path length would be small. Similarly, in the scenario with optical scattering being low, a ratio of the intensity of Raman light through the left aperture 82 ($I_l$) to the intensity of the Raman light through the middle aperture 84 ($I_m$) after correction for path length would also be small. Thus, when $I_r/I_m$ and $I_l/I_m$ are small, the optical scattering is low. The greater the scattering in the tissue, the greater the ratios of $I_r/I_m$ and $I_l/I_m$. It is also noted that the absorption of FIG. 2a would be generally approximate to the sum of the intensities ($I_r+I_m+I_l$).

Figure 2A:
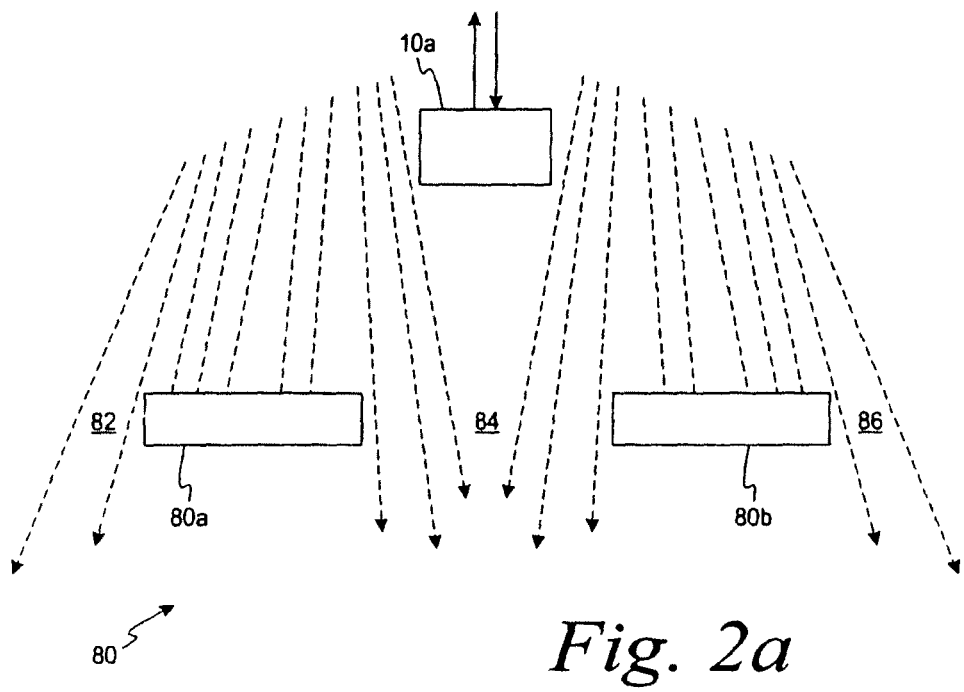
FIG. 2a is an illustration further detailing the spatial filter used in determining the analyte concentration of FIG. 1.

Using the apparatus of FIG. 2a, if the condition of the body tissue changes so as to affect the scattering properties of the tissue, then the spatial pattern of the Raman signals from the Raman-generating material would also subsequently change. By applying this relative change to a series of analyte measurements, the analyte signal is normalized against optical probe volume and, thus, increases the accuracy of the calculated analyte concentration.

Figure 2B:
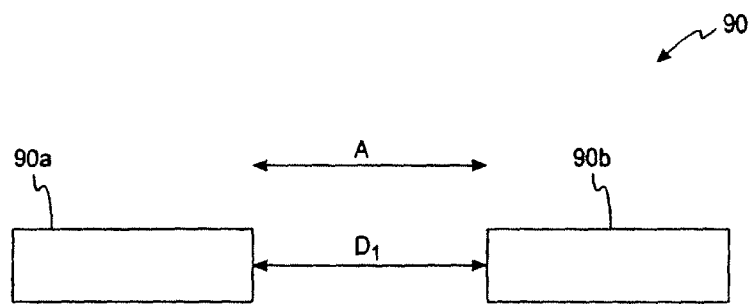
FIG. 2b, 2c depicts positions of a movable spatial filter according to one embodiment.
Figure 2C:
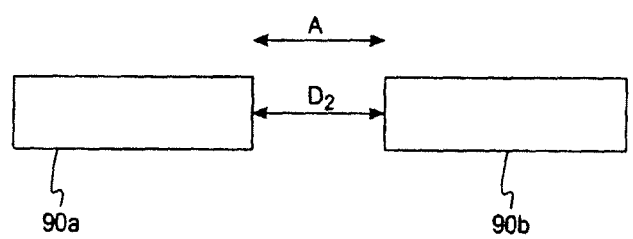

It is contemplated that the spatial filter may be adjustable to adjust the size of the aperture openings. This may be advantageous to discriminate scattered light from absorbed light. For example, referring to FIGS. 2b and 2c, a spatial filter 90 includes sections 90a and 90b. The sections 90a, 90b are movable along a generally horizontal direction in either direction (see arrow A). FIG. 2b depicts the sections 90a, 90b in a more open position such that the distance therebetween is represented by distance D1. FIG. 2c depicts the sections 90a, 90b in a more closed position such that the distance therebetween is represented by distance D2.

It is also contemplated that the spatial filter itself may be movable so as to better determine and characterize the scattered light. For example, the spatial filter may be moved to determine where the light propagates through the sample and/or to selectively measure multiple scattered or transmitted non-scattered light. If you excite a first point and measure at a second point with an aperture, then you have some idea of pathlength. By having a better idea of the pathlength, the tissue volume can be adjusted, if necessary, with respect to the analyte signal, which results in a more accurate analyte concentration.

Referring back to FIG. 1, after the Raman signals proceed through the spatial filter 80, the collection optics 18 collect the returned Raman signals 16, 20. It is contemplated that the collection optics may collect the Raman signals before they pass through the spatial filter. The spatial filter 80 in this method, however, needs to be located before the Raman signals are passed to a detector.

The collected Raman signals are then passed to a detector 30. The detector 30 assists in determining the analyte concentration (e.g., glucose) from the collected Raman signals. One example of a detector that may be used is a silicon detector. Other examples of detectors include an extended InGaAs detector, a germanium detector, a lead selenide (PbSe) detector, or a lead sulfide (PbS) detector. It is contemplated that other detectors may be employed to assist in determining the analyte concentration (e.g., glucose) from the collected Raman signals.

It is contemplated that a plurality of detectors and a plurality of apertures may be used. In this embodiment, the plurality of apertures and detectors may approximate a direct-imaging arrangement, which likely would provide a more accurate measure of scattering and absorption.

The corrections for Raman absorption and/or scattering properties of the body tissue related to quantifying analytes that have weak Raman signals (e.g., glucose in body tissue) may be accomplished by several methods. In one method, a calibration algorithm that incorporates absorption and/or scattering properties of the tissue to correct for the analyte concentration reading.

In another method, the collection times are automatically adjusted so that the appropriate signal-to-noise ratio is achieved, which assists in obtaining a more accurate analyte reading. For example, the collection times may be increased to increase the total amount of signals, which generally translates to better signals, especially with smaller signals.

By correcting or accounting for the optical absorbance and/or scattering in the skin tissue, the Raman signature of glucose can be quantitatively determined in a more accurate manner. Thus, this method provides an optical solution to correct quantitative, analytical signals for changes in the tissue optical properties.

Figure 3:
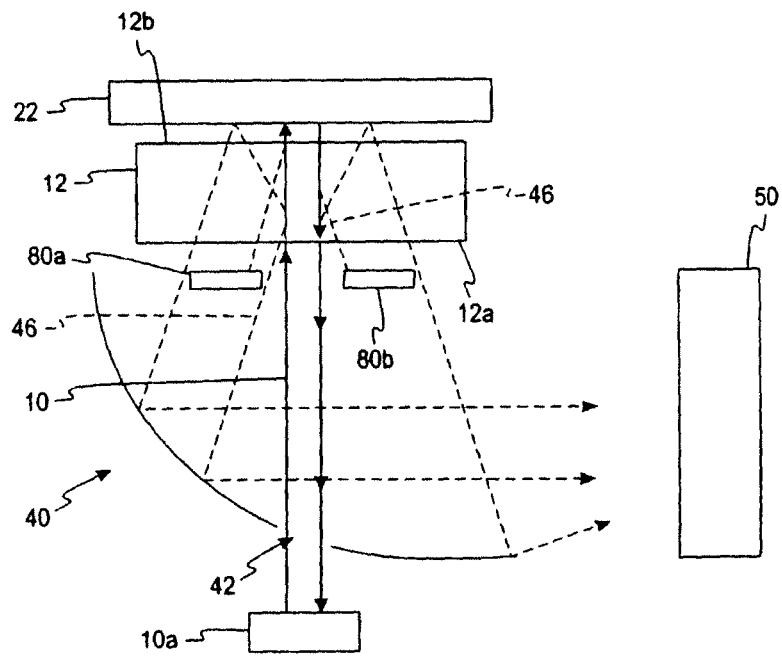
FIG. 3 is an illustration used in determining the analyte concentration using Raman spectral information according to another embodiment.

The collection optics may vary from that depicted in FIG. 1. FIG. 3 depicts an illustration similar to FIG. 1 that includes a parabolic mirror 40 in which the high-intensity light 10 passes through an opening 42 formed therein. The high-intensity light 10 enters the tissue and generates Raman signals, which scatter in all directions. The scattered Raman signals 46 are directed back to the parabolic mirror 40 after passing between or around the spatial filter sections 80a, 80b. The Raman signals are further reflected by the parabolic mirror to a detector 50 where the analyte concentration is determined from the collected Raman signals. The analyte concentration in this method may be corrected in a similar manner as discussed in connection with FIGS. 1 and 2.

According to another embodiment, the collection optics may be other mirrors with curvatures that deliver focused laser light back into the tissue. Alternatively, the collection optics may be other mirrors with curvatures that are shaped to deliver parallel light back into the tissue depending on the Raman signal collection optics.

Figure 4:
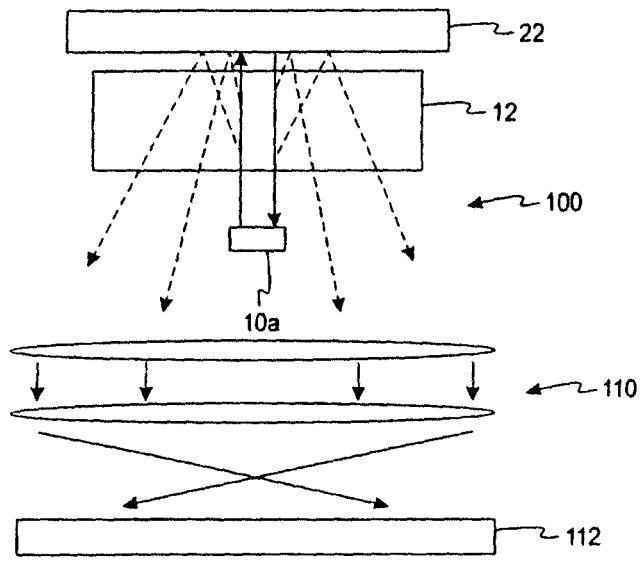
FIG. 4 is an illustration used in determining the analyte concentration using Raman spectral information according to another embodiment.

In another embodiment, the spatial distribution of the Raman signals may also be achieved by using an optical design based on spatial imaging. In this embodiment, a spatial filter is unnecessary. One such non-limiting example is shown in FIG. 4. FIG. 4 shows the high-intensity light source 10a, the skin issue 12, and the Raman-generating material 22. Raman signals 100 are collected by imaging optics 110 and then are directed to an array detector 112. The array detector 112 is an array of individuals detectors (pixels) that each measure a portion of Raman signal. The imaging optics and the detector, in one method, use the Raman signals to correct for both absorption and scattering caused by the tissue.

According to another method, a non-invasive method of determining the concentration of an analyte using Raman spectral information includes pinching an area of the skin tissue. An area of the skin tissue is pinched. A Raman-generating material is placed near or around the pinched skin tissue. The Raman-generating material forms at least one opening therethrough. A high-intensity, narrow band of light is applied to the skin tissue through the at least one opening. The high-intensity light enters the skin tissue and generates a Raman signal. The high-intensity light and Raman signal that pass through the pinched skin tissue are reflected back into the pinched skin tissue via the Raman-generating material. The Raman signal generated from the high-intensity light entering the skin tissue and the additional Raman signal generated from the Raman-generating material is collected. The analyte concentration is determined using the collected Raman signals.

Figure 5A:
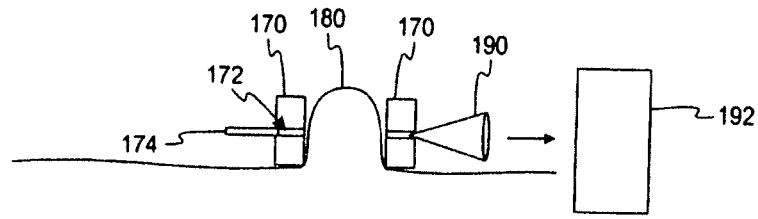
FIG. 5a is an illustration used in determining the analyte concentration using Raman spectral information according to a further embodiment.

As shown in FIG. 5a, a Raman-generating material 170 is placed near or around a pinched skin tissue 180. The width of the pinched skin tissue is generally from about 1 to about 2 mm. The Raman-generating material 170 forms at least one opening 172 in which the high-intensity light 174 is applied through the at least one opening 172. The high-intensity light 174 enters the pinched skin tissue 180 and generates a Raman signal. The high-intensity light and Raman signal that pass through the pinched skin tissue are reflected back into the pinched skin tissue via the Raman-generating material 170. Additionally, the Raman-generating material 170 generates an additional Raman signal. The Raman signals are collected and the analyte concentration is determined using the collected Raman signals.

Figure 5B:
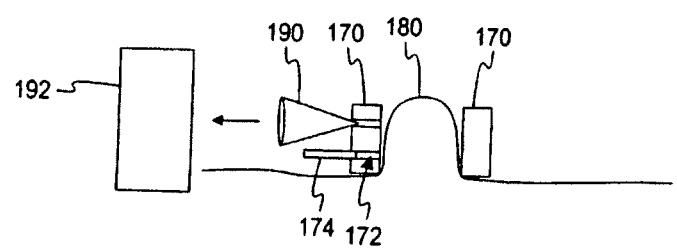
FIG. 5b is an illustration used in determining the analyte concentration using Raman spectral information according to a further embodiment.

The Raman signals may be collected via high NA (numerical aperture) optics or NA fiber(s) 190. The high NA (numerical aperture) optics or NA fiber(s) 190 transmit the collected Raman signals to a spectrometer 192. It is contemplated that the collected signals may be transmitted to a single detector with a filter, a CCD (cathode-coupled detector), a diode array, or other devices that detect a specific signal. It is contemplated that the Raman signals may be collected on the same side as the high-intensity light entering the pinched skin tissue such as shown, for example, in FIG. 5b.

In addition to determining analyte concentration, the Raman spectral information may be used in other methods. For example, in one method, information from the collected Raman signals may be used to perform a general diagnosis. The general diagnosis may include identifying (a) the presence of a particular analyte; (b) a particular molecule or (c) tissue morphology. The general diagnosis can be directed to several beneficial applications. For example, potential cancerous skin lesions may be identified in one application. By identifying potential cancerous cells, the tissue removal can be minimized. In another application, the stage of cancerous cells may be identified. In a further application, the effectiveness of cancer photodynamic therapy may be tracked. It is contemplated that other diagnosis may be performed using the inventive methods.

In addition to using Raman signals, other signals may be used in other methods. In another method, a non-invasive method for determining the concentration of an analyte uses fluorescence spectral information. Analytes that may be measured using fluorescence spectral information include glucose, lipid profiles (e.g., cholesterol, triglycerides, LDL and HDL), microalbumin, hemoglobin $A_{1C}$, or bilirubin. The present invention is not limited, however, to these specific analytes and it is contemplated that other analyte concentrations may be determined. The analytes may be in, for example, a whole blood sample, a blood serum sample, a blood plasma sample, and other body fluids like ISF (interstitial fluid) and urine.

The present invention assists in providing a method of correcting for optical absorbance and/or tissue scattering that can be transient during non-invasive analyte (e.g., glucose) detection. The fluorescence signature of analytes such as glucose can be corrected based on the optical absorbance and tissue scattering occurring in the tissue. The absorption of the skin tissue and tissue scattering may vary in the short term, as well as the long term as discussed above. According to another method, the analyte concentration is determined using fluorescence spectral information. A high-intensity band of light is applied to a first side of skin tissue. The high-intensity light enters the skin tissue and generates a fluorescence signal. A fluorescence-generating material is placed in a location nearest a second side of skin tissue. The second side is located generally opposite of the first side. The high-intensity light from the fluorescence-generating material is reflected so as to produce additional fluorescence signal that passes through the skin tissue towards the first side of the skin tissue. The fluorescence signal generated from the high-intensity light entering the skin tissue is reflected towards the first side of the skin tissue via the fluorescence-generating material. The fluorescence signal generated from the high-intensity light entering the skin tissue and the additional fluorescence signal generated from the fluorescence-generating material are collected. The analyte concentration is determined using information from the collected fluorescence signals.

Figure 6A:
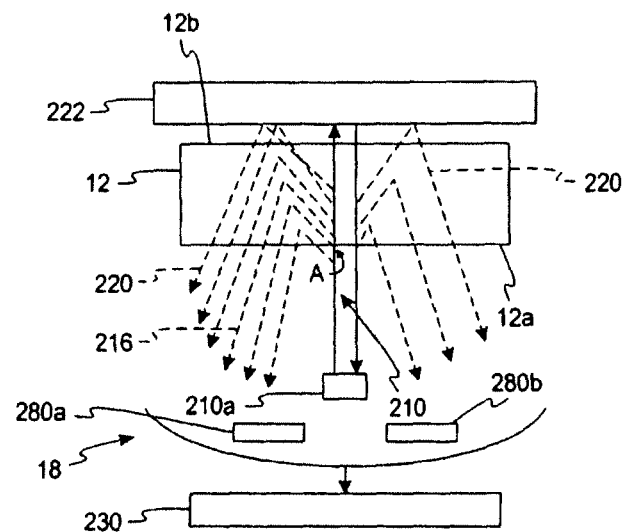
FIG. 6a is an illustration used in determining the concentration of an analyte using fluorescence spectral information according to another embodiment.

Referring to FIG. 6a, an illustration is used showing the location of the fluorescence-generating material and the high-intensity band of light according to one method. High-intensity light 210 is applied to the skin tissue 12 such as pinched skin tissue or a finger. The high-intensity light 210 is shown in FIG. 6a as coming from a high-intensity light source 210a. The high-intensity light 210 may be a narrow band of light, but does not necessarily have to be a narrow band of light. The high-intensity light source may come from a monochromatic light source. It is contemplated that other light sources may be used such as a light-emitting diode, incoherent lamps, a dye laser, gas laser, ion laser or a pumped laser.

The wavelength of the light source may vary but is generally between 300 and 10,000 nm. The fluorescence spectral information in one method may be collected in the wavelength range from about 300 nm to about 12,000 nm. It is contemplated that the fluorescence spectral information may be collected in different ranges depending on the analyte concentration to be determined.

The high-intensity light 210 enters on the first side 12a of the skin tissue 12. As shown in FIG. 6a, the high-intensity light 210 enters the skin tissue 12 at point A. After the high-intensity light 210 enters the skin tissue 12, a fluorescence signal is generated and scatters in all directions. A portion of the high-intensity light may contact the skin without entering the skin and scatter in all directions. A portion 216 of the fluorescence signal is redirected back towards the collection optics 18 after entering the skin tissue 12. Some of the fluorescence signal exits the skin tissue 12, however, and is reflected back using a fluorescence-generating material 222. The fluorescence-generating material 222 reflects back fluorescence signals towards the collection optics 18 that would otherwise have been lost exiting the other side 12b of the skin tissue 12, which is opposite of the collection optics 18. Thus, an increased fraction of the fluorescence signal will be redirected to the collection optics 18. It is contemplated that an increased fraction of the fluorescence signal may be redirected using a reflective surface such as a mirror. A portion of the fluorescence signal created by the fluorescence-generating material is scattered at oblique angles and will not be detected or may also be absorbed before being detected.

The fluorescence-generating material 222 is placed in a location nearest the other side 12b of the skin tissue 12. The fluorescence-generating material is located generally opposite of the entry of the applied high-intensity light. As shown in FIG. 6a, the fluorescence-generating material 222 is located opposite of the entry of the high-intensity light 210 at point A in FIG. 6a. It is contemplated that the fluorescence-generating material may be a single reflector as shown in FIG. 6a or a plurality of reflectors.

The fluorescence-generating material 222 also receives the high-intensity light 210 and generates additional fluorescence signal therefrom. To the extent that the fluorescence-generating material does not create fluorescence signals from the high-intensity light 210, the fluorescence-generating material 222 reflects back the remaining portion of the high-intensity light back through the skin tissue 12. These fluorescence signals will typically envelop a larger volume of skin tissue because the fluorescence signals will originate and scatter outwardly from every point in the skin tissue. After this high-intensity light is reflected back into the skin tissue 12 via the fluorescence-generating material 222, additional fluorescence signals may be generated. Thus, the optical pathlength is increased by passing the source light through the skin tissue twice. By increasing the optical pathlength, the resulting analytical signal is also increased.

Using the fluorescence-generating material 222, a measure of optical absorption can be obtained. Absorption is generally proportional to the total quantity of fluorescence signal from the fluorescence-generating material 222 that passes through the sample. In the case where the entire fluorescence signal can be integrated, then the analytical signal can be further corrected for changes in tissue absorbance and tissue scattering. In the case where the entire Raman signal can be integrated, then the analytical signal can be further corrected for changes in tissue absorbance and scattering. Changes in tissue absorbance and scattering may be caused by, for example, increased blood flow or changes in tissue hydration. For example, the intensity of the fluorescence signals from the fluorescence-generating material using only the high-intensity light can be compared to the intensity of the fluorescence signals using the fluorescence-generating material and the body tissue using the high-intensity light. A comparison of these intensities can determine and quantify the level of optical absorbance by the tissue.

Thus, in summary, the fluorescence-generating material 222 (a) reflects back fluorescence signal created on the initial pass through the skin tissue that otherwise would have been lost; (b) creates fluorescence signal from the high-intensity light 210; and (c) reflects back the light source that did not create a fluorescence signal back into the skin tissue with the possibility of forming an additional fluorescence signal. These fluorescence signals are designated generally in FIG. 6a as fluorescence signals 220.

The fluorescence-generating material may function under a fluorescence mechanism where light of a shorter wavelength excites the molecule and then the molecule fluoresces, giving off light of a longer wavelength. The fluorescence-generating material may be formed from a variety of materials such fluorescence dyes. The fluorescence dyes may be near-infrared (NIR) dyes, IR dyes and visible dyes. Some examples of NIR fluorescent dyes include derivatives from cyanine dyes (Cy5.5) or the clinically-approved indocyanine green (ICG). Such dyes are typically used as a coating since they are usually aqueous in nature. The dyes may be mobilized or impregnated in the fluorescence-generating material. It is contemplated that other materials may be used as a fluorescence-generating material that function in a similar manner.

Other materials that fluoresce in the NIR operate slightly differently. The material used in the NIR card functions on "photon upconversion" where light of a longer wavelength is absorbed by a first molecule and the energy is transferred to a second molecule that fluoresces at a shorter wavelength. This process is referred to upconversion since the excitation light is of lower energy than the emission light. One example is the use of quantum dots. Quantum dots are small metallic materials whose fluorescence is size dependent. It is contemplated that other materials may be used as a fluorescence-generating material that function in a similar manner.

It is contemplated that other materials may be used as the fluorescence-generating material that fluoresce in a different manner and in a different spectrum. The fluorescence-generating material to be used generates a unique fluorescence signal.

In one embodiment, the fluorescence-generating material may be a thin coating or layer on a thicker substrate, which is not a fluorescence-generating material. In another embodiment, the substrate may be formed entirely of the fluorescence-generating material.

Determining the concentration of an analyte (e.g., glucose) requires a measure proportional to the quantity of the analyte and a measure of the volume in which that quantity analyte resides. Employing a measure of optical scattering allows the analyte concentration calculation to be corrected should the optical probe volume change over the course of several measurements.

In one method, before collecting the fluorescence signals, a spatial filter is provided that measures the optical scattering of the fluorescence signals in the tissue. In one method, a spatial filter is placed to block a fraction of the fluorescence signals emerging from the skin tissue and to allow the remaining fraction of the fluorescence signals to strike the at least one detector. Thus, a spatial filter blocks light in one portion and allows light through in another portion. FIG. 6a depicts a spatial filter 280, which is shown in more detail in FIG. 6b. The spatial filter 280 includes a plurality of apertures 282, 284, 286 being formed. Sections 280a, 280b of the spatial filter 280 block a fraction of the fluorescence signals. If the optical scattering is low, the intensity (I) of the fluorescence signal at the middle aperture 284 would likely be significantly higher than the intensities of the fluorescence signals at outer apertures 282, 286 since a small fraction of the fluorescence signals would take a lateral trajectory through the skin tissue.

In the scenario with optical scattering being low, a ratio of the intensity of fluorescence light through the right aperture 286 ($I_r$) to the intensity of the fluorescence light through the middle aperture 284 ($I_m$) after correction for path length would be small. Similarly, in the scenario with optical scattering being low, a ratio of the intensity of fluorescence light through the left aperture 282 ($I_l$) to the intensity of the fluorescence light through the middle aperture 284 ($I_m$) after correction for path length would also be small. Thus, when $I_r/I_m$ and $I_l/I_m$ are small, the scattering is low. The greater the scattering in the tissue, the greater the ratios of $I_r/I_m$ and $I_l/I_m$. It is also noted that the absorption of FIG. 6b would be generally approximate to the sum of the intensities ($I_r+I_m+I_l$).

Figure 6B:
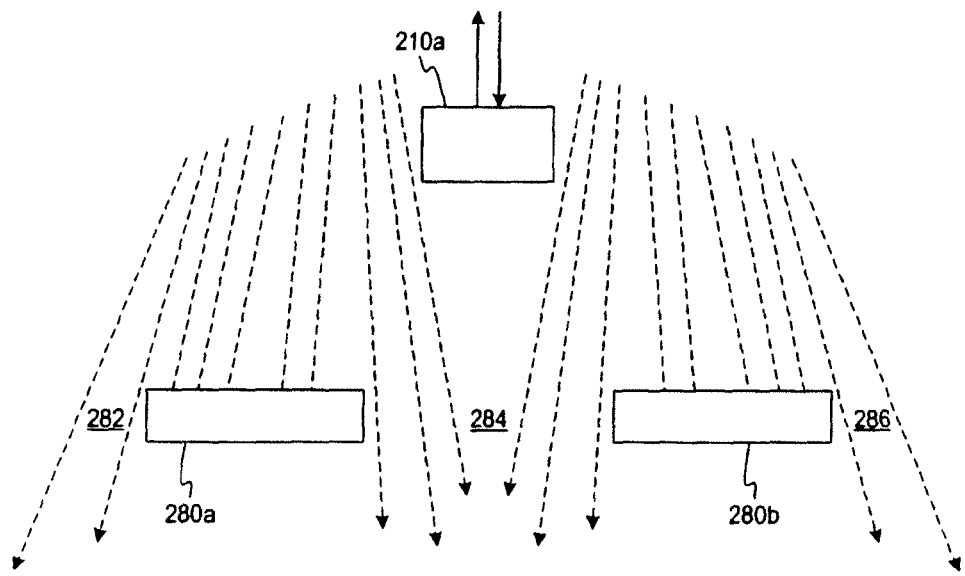

Using the apparatus of FIG. 6b, if the condition of the body tissue changes so as to affect the scattering properties of the tissue, then the spatial pattern of the fluorescence signals from the fluorescence-generating material would also subsequently change. By applying this relative change to a series of analyte measurements, the analyte signal is normalized against optical probe volume and, thus, increases the accuracy of the calculated analyte concentration.

It is contemplated that the spatial filter may be adjustable to adjust the size of the aperture openings as, for example, described above in the spatial filter 90. It is also contemplated that the spatial filter itself may be movable so as to better determine and locate the scatter.

The returned fluorescence signals 216, 220 are collected by the collection optics 18. The collected fluorescence signals are then passed to a detector 230. The detector 230 assists in determining the analyte concentration (e.g., glucose) from the collected fluorescence signals. One example of a detector of fluorescence signals that may be used is a silicon detector. Other examples of detectors include an extended InGaAs detector, a germanium detector, a lead selenide (PbSe) detector, or a lead (PbS) detector. It is contemplated that other detectors may be employed to assist in determining the analyte concentration (e.g., glucose) from the collected fluorescence signal.

It is contemplated that a plurality of detectors and a plurality of apertures may be used. In this embodiment, the plurality of apertures and detectors may approximate a direct-imaging arrangement, which likely would provide a more accurate measure of scattering and absorption.

The corrections for fluorescence absorption and/or scattering properties of the body tissue related to quantifying analytes that have weak fluorescence signals (e.g., glucose in body tissue) may be accomplished by several methods. In one method, a calibration algorithm that incorporates absorption and/or scattering properties of the tissue to correct for the analyte concentration reading.

In another method, the collection times are automatically adjusted so that the appropriate signal-to-noise ratio is achieved, which assists in obtaining a more accurate analyte reading. For example, the collection times may be increased to increase the total amount of signals, which generally translates to better signals, especially with smaller signals.

By correcting or accounting for the optical absorbance and/or scattering in the skin tissue, the fluorescence signature of glucose can be quantitatively determined in a more accurate manner. Thus, this method provides an optical solution to correct quantitative, analytical signals for changes in the tissue optical properties.

Figure 7:
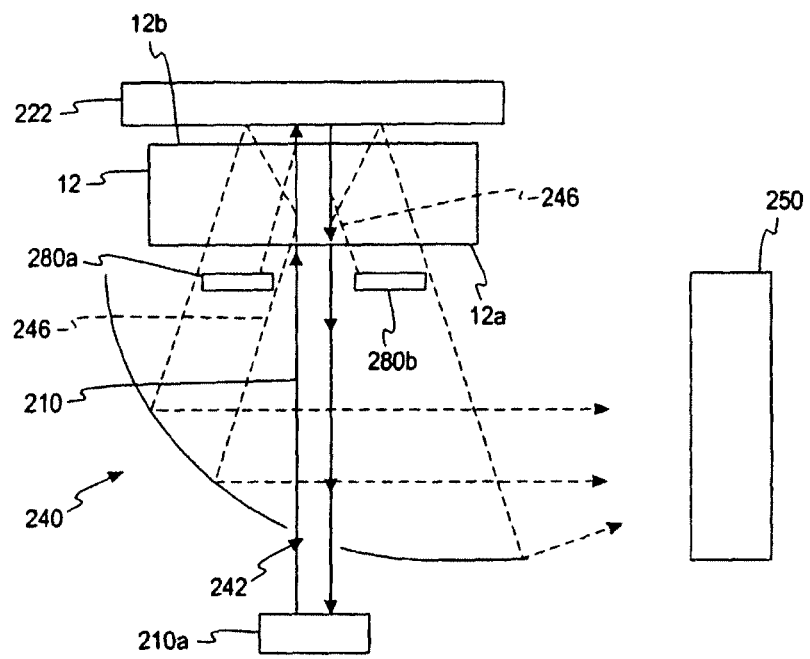
FIG. 7 is an illustration used in determining the analyte concentration using fluorescence spectral information according to a further embodiment.

The collection optics may vary from that depicted in FIG. 6a. FIG. 7 depicts an illustration similar to FIG. 6a that includes a parabolic mirror 240 in which the high-intensity light 210 passes through an opening 242 formed therein. The high-intensity light 210 enters the tissue and generates fluorescence signals, which scatter in all directions. The scattered fluorescence signals 246 are directed back to the parabolic mirror 240 after passing through the spatial filter sections 280a, 280b. The fluorescence signals are further reflected by the parabolic mirror to the detector 250 where the analyte concentration is determined from the collected fluorescence signals. The analyte concentration in this method may be corrected in a similar manner as discussed in connection with FIGS. 6a, 6b.

According to another embodiment, the collection optics may be other mirrors with curvatures that deliver focused laser light back into the tissue. Alternatively, the collection optics may be other mirrors with curvatures that are shaped to deliver parallel light back into the tissue depending on the fluorescence-signal collection optics.

Figure 8:
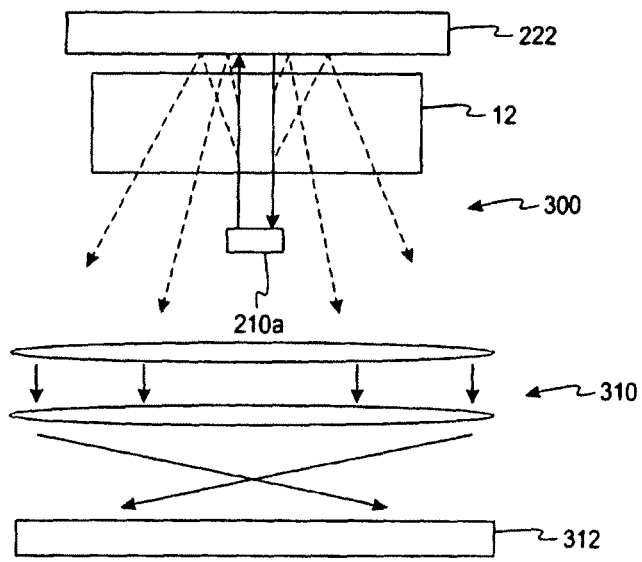
FIG. 8 is an illustration used in determining the analyte concentration using fluorescence spectral information according to yet another embodiment.

In another embodiment, the spatial distribution of the fluorescence signals may also be achieved by using an optical design based on spatial imaging. In this embodiment, a spatial filter is unnecessary. One such non-limiting example is shown in FIG. 8. FIG. 8 shows the high-intensity light source 210a, the skin issue 12, and the fluorescence-generating material 222. Fluorescence signals 300 are collected by imaging optics 310 and then are directed to the array detector 312. The array detector 312 is an array of individuals detectors (pixels) that each measure a portion of fluorescence signal. The imaging optics and the detector, in one method, use the fluorescence signals to correct for both absorption and scattering caused by the tissue.

Figure 9A:
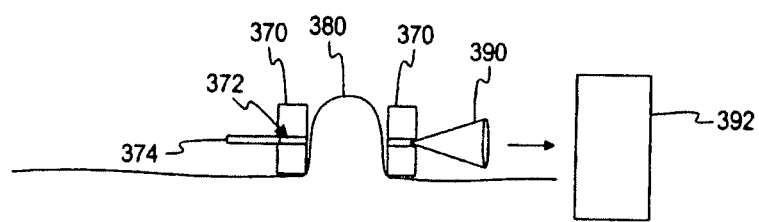
FIG. 9a is an illustration used in determining the analyte concentration using fluorescence spectral information according to a further embodiment.

As shown in FIG. 9a, a fluorescence-generating material 370 is placed near or around a pinched skin tissue 380. The width of the pinched skin tissue is generally from about 1 to about 2 mm. The fluorescence-generating material 370 forms at least one opening 372 in which the high-intensity light 374 is applied through the at least one opening 372. The high-intensity light 374 enters the pinched skin tissue 380 and generates a fluorescence signal. The high-intensity light and fluorescence signal that pass through the pinched skin tissue are reflected back into the pinched skin tissue via the fluorescence-generating material 370. Additionally, the fluorescence-generating material 370 generates an additional fluorescence signal. The fluorescence signals are collected and the analyte concentration is determined using the collected fluorescence signals.

Figure 9B:
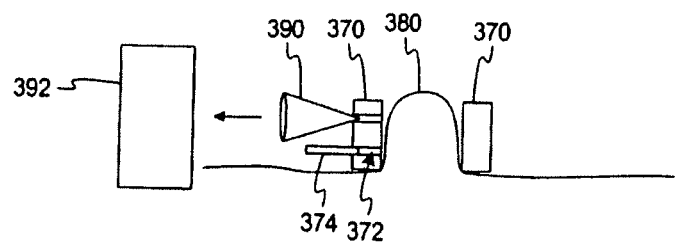
FIG. 9b is an illustration used in determining the analyte concentration using fluorescence spectral information according to a further embodiment.

The fluorescence signals may be collected via high NA (numerical aperture) optics or NA fiber(s) 390. The high NA (numerical aperture) optics or NA fiber(s) 390 transmit the collected fluorescence signals to a spectrometer 392. It is contemplated that the collected signals may be transmitted to a single detector with a filter, a CCD (cathode-coupled detector), a diode array, or other devices that detect a specific signal. It is contemplated that the fluorescence signals may be collected on the same side as the high-intensity light entering the pinched skin tissue such as shown, for example, in FIG. 9b.

In addition to determining analyte concentration, the fluorescence spectral information may be used in other methods. For example, in one method, information from the collected fluorescence signals may be used to perform a general diagnosis. The general diagnosis may include identifying (a) the presence of a particular analyte; (b) a particular molecule or (c) tissue morphology. The general diagnosis can be directed to several beneficial applications. For example, potential cancerous skin lesions may be identified in one application. By identifying potential cancerous cells, the tissue removal can be minimized. In another application, the stage of cancerous cells may be identified. In a further application, the effectiveness of cancer photodynamic therapy may be tracked. It is contemplated that other diagnosis may be performed using the inventive methods.

Process A

A non-invasive method of determining the concentration of an analyte using Raman spectral information, the method comprising the acts of:

applying a high-intensity, narrow band of light to a first side of skin tissue, the high-intensity light entering the skin tissue and generating a Raman signal;

placing a Raman-generating material in a location nearest a second side of the skin tissue, the second side being located generally opposite of the first side;

reflecting the high-intensity light from the Raman-generating material so as to produce additional Raman signal that passes through the skin tissue towards the first side of the skin tissue;

reflecting the Raman signal generated from the high-intensity light entering the skin tissue towards the first side of the skin tissue via the Raman-generating material;

collecting the Raman signal generated from the high-intensity light entering the skin tissue and the additional Raman signal generated from the Raman-generating material; and determining the analyte concentration using information from the collected Raman signals.

Process B

The method of Process A wherein the high-intensity light is applied from a monochromatic light source.

Process C

The method of Process B wherein the high-intensity light is applied from a laser-diode source.

Process D

The method of Process A wherein the high-intensity light is applied from a light-emitting diode, a zeon-arc lamp, a dye laser, a gas-laser source, an ion-laser source, or a pumped solid-state laser source.

Process E

The method of Process A wherein the analyte is glucose.

Process F

The method of Process A wherein the skin tissue is from about 1 to about 5 mm in thickness.

Process G

The method of Process A wherein the Raman-generated material is located opposite of the entry of the applied high-intensity light.

Process H

The method of Process A wherein the Raman-generated material includes a polymeric material.

Process I

The method of Process H wherein the polymeric material is polystyrene or polycarbonate.

Process J

The method of Process A further including a detector that assists in determining the analyte concentration.

Process K

The method of Process A wherein the Raman signal is collected using at least one parabolic mirror.

Process L

The method of Process A wherein the Raman signal is collected at a wavelength range of from about 300 to about 5000 nm.

Process M

The method of Process L wherein the Raman signal is collected a wavelength range of from about 830 to about 1030 nm.

Process N

The method of Process A wherein the high-intensity light is infrared light.

Process O

The method of Process A wherein the high-intensity light is near-infrared light.

Process P

The method of Process A wherein the high-intensity light is ultraviolet light.

Process Q

The method of Process A wherein the information from the collected Raman signals assists in determining the level of optical scattering and absorbance of the skin tissue, the information being used to assist in determining the analyte concentration.

Process R

The method of Process A wherein the information from the collected Raman signals assists in determining the level of optical scattering of the skin tissue, the information being used to assist in determining the analyte concentration.

Process S

The method of Process A wherein the information from the collected Raman signals assists in determining the level of absorbance of the skin tissue, the information being used to assist in determining the analyte concentration.

Process T

The method of Process A further including providing a spatial filter to assist in determining the level of absorbance of the skin tissue.

Process U

The method of Process A further including an array detector and imaging optics.

Process V

A non-invasive method of diagnosis using Raman spectral information, the method comprising the acts of:

applying a high-intensity, narrow band of light to a first side of skin tissue, the high-intensity light entering the skin tissue and generating a Raman signal;

placing a Raman-generating material in a location nearest a second side of the skin tissue, the second side being located generally opposite of the first side;

reflecting the high-intensity light from the Raman-generating material so as to produce additional Raman signal that passes through the skin tissue towards the first side of the skin tissue;

reflecting the Raman signal generated from the high-intensity light entering the skin tissue towards the first side of the skin tissue via the Raman-generating material;

collecting the Raman signal generated from the high-intensity light entering the skin tissue and the additional Raman signal generated from the Raman-generating material; and using information from the collected Raman signals to perform a general diagnosis.

Process W

The method of Process V wherein performing the general diagnosis includes identifying the presence of a particular analyte.

Process X

The method of Process V wherein performing the general diagnosis includes identifying a particular molecule.

Process Y

The method of Process V wherein the high-intensity light is applied from a monochromatic light source.

Process Z

The method of Process Y wherein the high-intensity light is applied from a laser-diode source.

Process AA

The method of Process V wherein the high-intensity light is applied from a light-emitting diode, a zeon-arc lamp, a dye laser, a gas-laser source, an ion-laser source, or a pumped solid-state laser source.

Process BB

The method of Process V wherein the analyte is glucose.

Process CC

The method of Process V wherein the skin tissue is from about 1 to about 5 mm in thickness.

Process DD

The method of Process V wherein the Raman-generated material is located opposite of the entry of the applied high-intensity light.

Process EE

The method of Process V wherein the Raman-generated material includes a polymeric material.

Process FF

The method of Process EE wherein the polymeric material is polystyrene or polycarbonate.

Process GG

The method of Process V further including a detector that assists in performing the general diagnosis.

Process HH

The method of Process V wherein the Raman signal is collected using at least one parabolic mirror.

Process II

The method of Process V wherein the Raman signal is collected at a wavelength range of from about 300 to about 5000 nm.

Process JJ

The method of Process II wherein the Raman signal is collected a wavelength range of from about 830 to about 1030 nm.

Process KK

The method of Process V wherein the high-intensity light is infrared light.

Process LL

The method of Process V wherein the high-intensity light is near-infrared light.

Process MM

The method of Process V wherein the high-intensity light is ultraviolet light.

Process NN

The method of Process V wherein the information from the collected Raman signals assists in determining the level of optical scattering and absorbance of the skin tissue, the information being used to assist in performing the general diagnosis.

Process OO

The method of Process V wherein the information from the collected Raman signals assists in determining the level of optical scattering of the skin tissue, the information being used to assist in performing the general diagnosis.

Process PP

The method of Process V wherein the information from the collected Raman signals assists in determining the level of absorbance of the skin tissue, the information being used to assist in determining the analyte concentration.

Process QQ

The method of Process V further including providing a spatial filter to assist in determining the level of absorbance of the skin tissue.

Process RR

The method of Process V further including an array detector and imaging optics.

Process SS

A non-invasive method of determining the concentration of an analyte using Raman spectral information, the method comprising the acts of:

pinching an area of the skin tissue;

placing a Raman-generating material near or around the pinched skin tissue, the Raman-generating material forming at least one opening therethrough;

applying a high-intensity, narrow band of light to the skin tissue through the at least one opening, the high-intensity light entering the skin tissue and generating a Raman signal;

reflecting the high-intensity light and Raman signal that pass through the pinched skin tissue back into the pinched skin tissue via the Raman-generating material;

collecting the Raman signal generated from the high-intensity light entering the skin tissue and the additional Raman signal generated from the Raman-generating material; and determining the analyte concentration using the collected Raman signals.

Process TT

The method of Process SS wherein the Raman signal is collected a wavelength range of from about 300 to about 5000 nm.

Process UU

The method of Process TT wherein the Raman signal is collected a wavelength range of from about 830 to about 1030 nm.

Process VV

The method of Process SS wherein the analyte is glucose.

Process WW

The method of Process SS wherein the Raman-generated material includes a polymeric material.

Process XX

A non-invasive method of determining the concentration of an analyte using fluorescence spectral information, the method comprising the acts of:

applying a high-intensity, narrow band of light to a first side of skin tissue, the high-intensity light entering the skin tissue and generating a fluorescence signal;

placing a fluorescence-generating material in a location nearest a second side of the skin tissue, the second side being located generally opposite of the first side;

reflecting the high-intensity light from the fluorescence-generating material so as to produce additional fluorescence signal that passes through the skin tissue towards the first side of the skin tissue;

reflecting the fluorescence signal generated from the high-intensity light entering the skin tissue towards the first side of the skin tissue via the fluorescence-generating material;

collecting the fluorescence signal generated from the high-intensity light entering the skin tissue and the additional fluorescence signal generated from the fluorescence-generating material; and determining the analyte concentration using information from the collected fluorescence signals.

Process YY

The method of Process XX wherein the high-intensity light is applied from a monochromatic light source.

Process ZZ

The method of Process YY wherein the high-intensity light is applied from a laser-diode source.

Process AAA

The method of Process XX wherein the high-intensity light is applied from a light-emitting diode or a zeon-arc lamp.

Process BBB

The method of Process XX wherein the high-intensity light is applied from a dye laser, a gas-laser source, an ion-laser source, or a pumped solid-state laser source.

Process CCC

The method of Process XX wherein the skin tissue is from about 1 to about 5 mm in thickness.

Process DDD

The method of Process XX wherein the fluorescence-generated material is located opposite of the entry of the applied high-intensity light.

Process EEE

The method of Process XX wherein the fluorescence-generated material includes a fluorescence dye.

Process FFF

The method of Process XX wherein the fluorescence-generated material includes quantum dots.

Process GGG

The method of Process XX further including a detector that assists in determining the analyte concentration.

Process HHH

The method of Process XX wherein the fluorescence signal is collected using at least one parabolic mirror.

Process III

The method of Process XX wherein the fluorescence signal is collected at a wavelength range of from about 300 to about 5000 nm.

Process JJJ

The method of Process III wherein the fluorescence signal is collected a wavelength range of from about 830 to about 1030 nm.

Process KKK

The method of Process XX wherein the high-intensity light is infrared light.

Process LLL

The method of Process XX wherein the high-intensity light is near infrared light.

Process MMM

The method of Process XX wherein the high-intensity light is ultraviolet light.

Process NNN

The method of Process XX wherein the information from the collected fluorescence signals assists in determining the level of optical scattering and absorbance of the skin tissue, the information being used to assist in determining the analyte concentration.

Process OOO

The method of Process XX wherein the information from the collected fluorescence signals assists in determining the level of optical scattering of the skin tissue, the information being used to assist in determining the analyte concentration.

Process PPP

The method of Process XX wherein the information from the collected fluorescence signals assists in determining the level of absorbance of the skin tissue, the information being used to assist in determining the analyte concentration.

Process QQQ

The method of Process XX further including providing a spatial filter to assist in determining the level of absorbance of the skin tissue.

Process RRR

The method of Process XX further including an array detector and imaging optics.

Process SSS

A non-invasive method of diagnosis using fluorescence spectral information, the method comprising the acts of:

applying a high-intensity light to a first side of skin tissue, the high-intensity light entering the skin tissue and generating a fluorescence signal;

placing a fluorescence-generating material in a location nearest a second side of the skin tissue, the second side being located generally opposite of the first side;

reflecting the high-intensity light from the fluorescence-generating material so as to produce additional fluorescence signal that passes through the skin tissue towards the first side of the skin tissue;

reflecting the fluorescence signal generated from the high-intensity light entering the skin tissue towards the first side of the skin tissue via the fluorescence-generating material;

collecting the fluorescence signal generated from the high-intensity light entering the skin tissue and the additional fluorescence signal generated from the fluorescence-generating material; and using information from the collected fluorescence signals to perform a general diagnosis.

Process TTT

The method of Process SSS wherein performing the general diagnosis includes identifying the presence of a particular analyte.

Process UUU

The method of Process SSS wherein performing the general diagnosis includes identifying a particular molecule.

Process VVV

The method of Process SSS wherein the high-intensity light is a narrow band of light.

Process WWW

The method of Process SSS wherein the high-intensity light is applied from a laser-diode source.

Process XXX

The method of Process SSS wherein the high-intensity light is applied from a light-emitting diode or a zeon-arc lamp.

Process YYY

The method of Process SSS wherein the high-intensity light is applied from a dye laser, a gas-laser source, an ion-laser source, or a pumped solid-state laser source.

Process ZZZ

The method of Process SSS wherein the skin tissue is from about 1 to about 5 mm in thickness.

Process AAAA

The method of Process SSS wherein the fluorescence-generated material is located opposite of the entry of the applied high-intensity light.

Process BBBB

The method of Process SSS wherein the fluorescence-generated material includes a fluorescence dye.

Process CCCC

The method of Process SSS wherein the fluorescence-generated material includes quantum dots.

Process DDDD

The method of Process SSS further including a detector that assists in determining the analyte concentration.

Process EEEE

The method of Process SSS wherein the fluorescence signal is collected using at least one parabolic mirror.

Process FFFF

The method of Process SSS wherein the fluorescence signal is collected at a wavelength range of from about 300 to about 5000 nm.

Process GGGG

The method of Process FFFF wherein the fluorescence signal is collected a wavelength range of from about 830 to about 1030 nm.

Process HHHH

The method of Process SSS wherein the information from the collected Raman signals assists in determining the level of optical scattering and absorbance of the skin tissue, the information being used to assist in determining the analyte concentration.

Process IIII

The method of Process SSS wherein the information from the collected Raman signals assists in determining the level of optical scattering of the skin tissue, the information being used to assist in determining the analyte concentration.

Process JJJJ

The method of Process SSS wherein the information from the collected Raman signals assists in determining the level of absorbance of the skin tissue, the information being used to assist in determining the analyte concentration.

Process KKKK

The method of Process SSS further including providing a spatial filter to assist in determining the level of absorbance of the skin tissue.

Process LLLL

The method of Process SSS further including an array detector and imaging optics.

Process MMMM

A non-invasive method of determining the concentration of an analyte using fluorescence spectral information, the method comprising the acts of:
  pinching an area of the skin tissue;
  placing a fluorescence-generating material near or around the pinched skin tissue, the fluorescence-generating material forming at least one opening therethrough;
  applying a high-intensity, narrow band of light to the skin tissue through the at least one opening, the high-intensity light entering the skin tissue and generating a fluorescence signal;
  reflecting the high-intensity light and fluorescence signal that pass through the pinched skin tissue back into the pinched skin tissue via the fluorescence-generating material;
  collecting the fluorescence signal generated from the high-intensity light entering the skin tissue and the additional fluorescence signal generated from the fluorescence-generating material; and
  determining the analyte concentration using the collected fluorescence signals.

Process NNNN

The method of Process MMMM wherein the fluorescence signal is collected a wavelength range of from about 300 to about 5000 nm.

Process OOOO

The method of Process NNNN wherein the fluorescence signal is collected a wavelength range of from about 830 to about 1030 nm.

Process PPPP

The method of Process MMMM wherein the analyte is glucose.

While the present invention has been described with reference to one or more particular embodiments, those skilled in the art will recognize that many changes may be made thereto without departing from the spirit and scope of the present invention. Each of these embodiments, and obvious variations thereof, is contemplated as falling within the spirit and scope of the invention as defined by appended claims.

What is claimed is:

1. A non-invasive method of determining the concentration of an analyte using Raman spectral information, the method comprising the acts of:
  applying a high-intensity, narrow band of light to a first side of tissue, the high-intensity light entering the tissue at a first side and generating a Raman signal;
  providing a Raman-generating material adapted to generate Raman signals;
  reflecting the high-intensity light from the Raman-generating material so as to produce an additional Raman signal that passes towards the first side of the tissue;
  reflecting the Raman signal generated from the high-intensity light entering the tissue towards the first side of the tissue via the Raman-generating material;
  collecting the Raman signal generated from the high-intensity light entering the tissue and the additional Raman signal generated from the Raman-generating material; and
  determining the analyte concentration using information from the collected Raman signals.

2. The method of claim 1, wherein the high-intensity light is applied from a monochromatic light source.

3. The method of claim 2, wherein the high-intensity light is applied from a laser-diode source.

4. The method of claim 1, wherein the analyte is glucose.

5. The method of claim 1, wherein the Raman signal is collected at a wavelength range of from about 300 to about 5000 nm.

6. The method of claim 5, wherein the Raman signal is collected at a wavelength range of from about 830 to about 1030 nm.

7. The method of claim 1, wherein the information from the collected Raman signals assists in determining the level of optical scattering and absorbance of the tissue, the information being used to assist in determining the analyte concentration.

8. The method of claim 1, wherein the information from the collected Raman signals assists in determining the level of optical scattering of the tissue, the information being used to assist in determining the analyte concentration.

9. The method of claim 1, wherein the information from the collected Raman signals assists in determining the level of absorbance of the tissue, the information being used to assist in determining the analyte concentration.

10. The method of claim 1 further including a spatial filter for blocking Raman signals in one portion from being collected and for allowing Raman signals in another portion to be collected.

11. The method of claim 10, wherein the spatial filter includes a plurality of apertures.

12. The method of claim 11, wherein determining the analyte concentration further includes using information from the optical scattering of the Raman signals through the plurality of apertures.

13. The method of claim 10, wherein the spatial filter includes at least two sections that are moveable with respect to each other.

14. A non-invasive method of diagnosis using Raman spectral information, the method comprising the acts of:
applying a high-intensity, narrow band of light to a first side of tissue, the high-intensity light entering the tissue at a first side and generating a Raman signal;
providing a Raman-generating material adapted to generate Raman signals;
reflecting the high-intensity light from the Raman-generating material so as to produce an additional Raman signal that passes towards the first side of the tissue;
reflecting the Raman signal generated from the high-intensity light entering the tissue towards the first side of the tissue via the Raman-generating material;
collecting the Raman signal generated from the high-intensity light entering the tissue and the additional Raman signal generated from the Raman-generating material; and
using information from the collected Raman signals to perform a general diagnosis.

15. The method of claim 14, wherein performing the general diagnosis includes identifying the presence of a particular analyte.

16. The method of claim 14, wherein performing the general diagnosis includes identifying a particular molecule.

17. The method of claim 14, wherein the Raman signal is collected at a wavelength range of from about 300 to about 5000 nm.

18. The method of claim 17, wherein the Raman signal is collected at a wavelength range of from about 830 to about 1030 nm.

19. The method of claim 14, wherein the information from the collected Raman signals assists in determining the level of optical scattering and absorbance of the skin tissue, the information being used to assist in performing the general diagnosis.

20. The method of claim 14, wherein the information from the collected Raman signals assists in determining the level of optical scattering of the tissue, the information being used to assist in performing the general diagnosis.

21. The method of claim 14, wherein the information from the collected Raman signals assists in determining the level of absorbance of the tissue, the information being used to assist in performing the general diagnosis.

22. The method of claim 14 further including a spatial filter for blocking Raman signals in one portion from being collected and for allowing Raman signals in another portion to be collected.

23. The method of claim 22, wherein the spatial filter includes a plurality of apertures.

24. The method of claim 23, wherein performing the general diagnosis further includes using information from the optical scattering of the Raman signals through the plurality of apertures.

25. The method of claim 22, wherein the spatial filter includes at least two sections that are moveable with respect to each other.

26. A non-invasive method of determining the concentration of an analyte using fluorescence spectral information, the method comprising the acts of:
applying a high-intensity, narrow band of light to a first side of tissue, the high-intensity light entering the tissue at a first side and generating a fluorescence signal;
providing a fluorescence-generating material adapted to generate fluorescence signals;
reflecting the high-intensity light from the fluorescence-generating material so as to produce an additional fluorescence signal towards the first side of the tissue;
reflecting the fluorescence signal generated from the high-intensity light entering the tissue towards the first side of the tissue via the fluorescence-generating material;
collecting the fluorescence signal generated from the high-intensity light entering the tissue and the additional fluorescence signal generated from the fluorescence-generating material; and
determining the analyte concentration using information from the collected fluorescence signals.

27. The method of claim 26, wherein the analyte is glucose.

28. The method of claim 26, wherein the information from the collected fluorescence signals assists in determining the level of optical scattering and absorbance of the tissue, the information being used to assist in determining the analyte concentration.

29. The method of claim 26, wherein the information from the collected fluorescence signals assists in determining the level of optical scattering of the tissue, the information being used to assist in determining the analyte concentration.

30. The method of claim 26, wherein the information from the collected fluorescence signals assists in determining the level of absorbance of the tissue, the information being used to assist in determining the analyte concentration.

31. The method of claim 26 further including a spatial filter for blocking fluorescence signals in one portion from being collected and for allowing fluorescence signals in another portion to be collected.

32. The method of claim 31, wherein the spatial filter includes a plurality of apertures.

33. The method of claim 32, wherein determining the analyte concentration further includes using information from the optical scattering of the fluorescence signals through the plurality of apertures.

34. The method of claim 31, wherein the spatial filter includes at least two sections that are moveable with respect to each other.

35. A non-invasive method of diagnosis using fluorescence spectral information, the method comprising the acts of:
applying a high-intensity light to a first side of tissue, the high-intensity light entering the tissue at a first side and generating a fluorescence signal;
providing a fluorescence-generating material adapted to generate fluorescence signals;
reflecting the high-intensity light from the fluorescence-generating material so as to produce additional fluorescence signal that passes towards the first side of the tissue;
reflecting the fluorescence signal generated from the high-intensity light entering the tissue towards the first side of the tissue via the fluorescence-generating material;
collecting the fluorescence signal generated from the high-intensity light entering the tissue and the additional fluorescence signal generated from the fluorescence-generating material; and
using information from the collected fluorescence signals to perform a general diagnosis.

36. The method of claim 35, wherein the information from the collected fluorescence signals assists in determining the level of optical scattering and absorbance of the tissue, the information being used to assist in performing the general diagnosis.

37. The method of claim 35, wherein the information from the collected fluorescence signals assists in determining the level of optical scattering of the tissue, the information being used to assist in performing the general diagnosis.

38. The method of claim 35, wherein the information from the collected fluorescence signals assists in determining the level of absorbance of the tissue, the information being used to assist in performing the general diagnosis.

39. The method of claim 35 further including a spatial filter for blocking fluorescence signals in one portion from being collected and for allowing fluorescence signals in another portion to be collected.

40. The method of claim 39, wherein the spatial filter includes a plurality of apertures.

41. The method of claim 40, wherein performing the general diagnosis further includes using information from the optical scattering of the fluorescence signals through the plurality of apertures.

42. The method of claim 39, wherein the spatial filter includes at least two sections that are moveable with respect to each other.

43. A non-invasive method of determining the concentration of an analyte using Raman spectral information, the method comprising the acts of:
   pinching an area of skin tissue;
   placing a Raman-generating material near or around the pinched skin tissue, the Raman-generating material forming at least one opening therethrough;
   applying a high-intensity, narrow band of light to the skin tissue through the at least one opening, the high-intensity light entering the pinched skin tissue and generating a Raman signal;
   reflecting the high-intensity light and Raman signal that pass through the pinched skin tissue back into the pinched skin tissue via the Raman-generating material;
   collecting the Raman signal generated from the high-intensity light entering the skin tissue and an additional Raman signal generated from the Raman-generating material; and
   using information from the collected Raman signals to perform a general diagnosis.

44. The method of claim 43, wherein performing the general diagnosis includes identifying the presence of a particular analyte.

45. The method of claim 43, wherein performing the general diagnosis includes identifying a particular molecule.

46. The method of claim 43, wherein the Raman signal is collected at a wavelength range of from about 300 to about 5000 nm.

47. The method of claim 46, wherein the Raman signal is collected at a wavelength range of from about 830 to about 1030 nm.

48. A non-invasive method of determining the concentration of an analyte using fluorescence spectral information, the method comprising the acts of:
   pinching an area of skin tissue;
   placing a fluorescence-generating material near or around the pinched skin tissue, the fluorescence-generating material forming at least one opening therethrough;
   applying a high-intensity narrow band of light to the skin tissue through the at least one opening, the high-intensity light entering the pinched skin tissue and generating a fluorescence signal;
   reflecting the high-intensity light and fluorescence signal that pass through the pinched skin tissue back into the pinched skin tissue via the fluorescence-generating material;
   collecting the fluorescence signal generated from the high-intensity light entering the skin tissue and an additional fluorescence signal generated from the fluorescence-generating material; and
   using information from the collected fluorescence signals to perform a general diagnosis.

49. The method of claim 48, wherein performing the general diagnosis includes identifying the presence of a particular analyte.

50. The method of claim 48, wherein performing the general diagnosis includes identifying a particular molecule.

51. A non-invasive method of determining the concentration of an analyte using fluorescence spectral information, the method comprising the acts of:
   pinching an area of skin tissue;
   placing a fluorescence-generating material near or around the pinched skin tissue, the fluorescence-generating material forming at least one opening therethrough;
   applying a high-intensity narrow band of light to the skin tissue through the at least one opening, the high-intensity light entering the pinched skin tissue and generating a fluorescence signal;
   reflecting the high-intensity light and fluorescence signal that pass through the pinched skin tissue back into the pinched skin tissue via the fluorescence-generating material;
   collecting the fluorescence signal generated from the high-intensity light entering the skin tissue and an additional fluorescence signal generated from the fluorescence-generating material; and
   determining the analyte concentration using information from the collected fluorescence signals.

52. The method of claim 51, wherein the analyte is glucose.

* * * * *